United States Patent
Zhang et al.

(10) Patent No.: US 11,667,597 B2
(45) Date of Patent: Jun. 6, 2023

(54) METHOD FOR LINKAGE RECOVERY OF ORGANIC ACID IN AQUEOUS ORGANIC ACID SOLUTION

(71) Applicant: GUANGZHOU YINNOVATOR BIOTECH CO., LTD., Guangzhou (CN)

(72) Inventors: Ruizhe Zhang, Guangzhou (CN); Yunsi Liu, Guangzhou (CN)

(73) Assignee: GUANGZHOU YINNOVATOR BIOTECH CO., LTD., Guangzhou (CN)

( * ) Notice: Subject to any disclaimer, the term of this patent is extended or adjusted under 35 U.S.C. 154(b) by 0 days.

(21) Appl. No.: 17/257,375

(22) PCT Filed: Sep. 26, 2019

(86) PCT No.: PCT/CN2019/108187
§ 371 (c)(1),
(2) Date: Dec. 31, 2020

(87) PCT Pub. No.: WO2020/108066
PCT Pub. Date: Jun. 4, 2020

(65) Prior Publication Data
US 2021/0122695 A1  Apr. 29, 2021

(30) Foreign Application Priority Data
Nov. 26, 2018 (CN) .......................... 201811418227.2

(51) Int. Cl.
*C07C 51/48* (2006.01)
*C07C 51/46* (2006.01)
*C07C 51/42* (2006.01)
*C07C 49/303* (2006.01)
*C07F 9/113* (2006.01)
*C07C 53/02* (2006.01)
*C07C 53/08* (2006.01)

(52) U.S. Cl.
CPC ............ *C07C 51/48* (2013.01); *C07C 49/303* (2013.01); *C07C 51/42* (2013.01); *C07C 51/46* (2013.01); *C07F 9/113* (2013.01); *C07C 53/02* (2013.01); *C07C 53/08* (2013.01)

(58) Field of Classification Search
None
See application file for complete search history.

(56) References Cited

U.S. PATENT DOCUMENTS

| 3,024,170 | A | * | 3/1962 | Othmer | .................... | B01D 3/36 |
| | | | | | | 203/67 |
| 4,143,066 | A | * | 3/1979 | Kalcevic | ................. | C07C 51/44 |
| | | | | | | 203/16 |
| 4,447,643 | A | * | 5/1984 | Feldman | ................. | C07C 29/86 |
| | | | | | | 568/699 |
| 4,735,690 | A | * | 4/1988 | Berg | ....................... | C07C 51/44 |
| | | | | | | 203/61 |
| 5,173,156 | A | * | 12/1992 | Berg | ....................... | C07C 51/46 |
| | | | | | | 203/61 |
| 5,399,751 | A | * | 3/1995 | Gentry | ..................... | C07C 51/42 |
| | | | | | | 203/16 |
| 5,409,579 | A | * | 4/1995 | Gualy | ..................... | C07C 51/48 |
| | | | | | | 203/16 |
| 5,662,780 | A | | 9/1997 | Sasaki et al. | | |

FOREIGN PATENT DOCUMENTS

| CN | 101792386 A | | 8/2010 |
| CN | 102344353 A | | 2/2012 |
| CN | 106397184 | * | 2/2017 |
| CN | 106397184 A | | 2/2017 |
| CN | 109384666 | | 2/2019 |
| JP | S48013090 B | | 2/1973 |
| JP | H11228486 | | 8/1999 |
| JP | 2009000686 A | | 1/2009 |
| JP | 2015140342 A | | 8/2015 |

OTHER PUBLICATIONS

Machine generated English language translation of CN 102344353 (published Feb. 8, 2012) (Year: 2012).*
Zhang ("Adsorptive Separation of Acetic Acid from Dilute Aqueous Solutions: Adsorption Kinetic, Isotherms, and Thermodynamic Studies" J. Chem. Eng. Data 2016, 61, p. 213-219) (Year: 2016).*
Chinese-language International Search Report and Written Opinion issued in counterpart PCT Application No. PCT/CN2019/108187 dated Nov. 28, 2019, with English translation (eleven (11) pages).
Chinese-language Office Action issued in counterpart CN Application No. 201811418227.2 dated Apr. 1, 2020, with English translation (thirteen (13) pages).
First Search of CN Prior Application issued in counterpart CN Application No. 201811418227.2 (two (2) pages), Apr. 1, 2020.
Japanese-language Office Action issued in counterpart JP Application No. 2021-525359 dated Feb. 25, 2022, with English translation (twelve (12) pages).

* cited by examiner

*Primary Examiner* — Amy C Bonaparte
(74) *Attorney, Agent, or Firm* — David S. Bradin; Nexsen Pruet, PLLC

(57) ABSTRACT

Disclosed is a method for linkage recovery of an organic acid in an aqueous organic acid solution. The method comprises: mixing a solution with an organic acid concentration lower than 20 wt % with a specific extractant and then subjecting same to counter-current extraction so as to obtain an extract phase and a raffinate phase; and subjecting the extract phase together with a solution with an acid concentration higher than 70 wt % to an azeotropic rectification so as to recover an organic acid. When the concentration of the aqueous organic acid solution is 20 wt %-70 wt %, the aqueous organic acid solution is extracted and concentrated to make the concentration of the aqueous organic acid solution higher than 70 wt %.

17 Claims, No Drawings

METHOD FOR LINKAGE RECOVERY OF ORGANIC ACID IN AQUEOUS ORGANIC ACID SOLUTION

CROSS REFERENCE TO RELATED APPLICATIONS

This application is a 35 U.S.C. § 371 U.S. national phase entry of International Application No. PCT/CN2019/108187 having an international filing date of Sep. 26, 2019, which claims the benefit of Chinese Application No. 201811418227.2 filed Nov. 26, 2018, the contents of each of which are incorporated herein by reference in their entireties.

TECHNICAL FIELD

The present application belongs to the field of solution treatment, and relates to a method for recovery of an organic acid in a solution, for example, to a method for linkage recovery of an organic acid in an aqueous organic acid solution.

BACKGROUND

Organic acids are important organic chemical raw materials widely applied to industries such as basic organic synthesis, medicine, dyes, perfumes, and pesticides, and form a water-organic acid system, which is a highly non-ideal system, during or after the production. Organic acids are corrosive and have high requirements on equipments, but there is still no ideal method for recovering an organic acid.

For a low-concentration aqueous organic acid solution, an organic acid in wastewater of traditional pharmaceutical companies generally has a concentration lower than 20% and tends to be dissolved in water. If the organic acid is recovered by a rectification method, the rectification process requires huge steam consumption and high recovery costs due to a high water content. The organic acid may also be neutralized in some traditional processes by adding a base in wastewater. Most of organic acid salts formed therefrom are not recovered, and only the wastewater can be treated, so that organic acid products cannot be obtained. Even if a small number of companies recover the organic acid salts, the process is complicated and the recovery costs are high, which is generally a last resort. Moreover, from the perspective of the degree of separation, a membrane separation method has a good effect. However, the large-scale industrial production of membranes is difficult due to the stability and regeneration problems of the membranes, resulting in high recovery costs. An adsorption method has low energy consumption and a small adsorption capacity, and is not applied to the industry for a difficulty in subsequent treatment. An esterification method has mature processes and a large production capability, but the processes are relatively complicated, and the generated waste sulfuric acids cause secondary pollution. Therefore, there is substantially no good recovery method for such dilute organic acids in the industry.

For a high-concentration aqueous organic acid solution, an organic acid with a mass fraction greater than 80% may be directly recovered through azeotropic rectification. An aqueous organic acid solution with a concentration lower than 50% needs to be extracted and concentrated in advance to increase the concentration, and then subjected to azeotropic rectification. However, a problem in the azeotropic rectification is a necessity to add an azeotropic agent to the aqueous organic acid solution to form an azeotrope of water and the azeotropic agent, such that during rectification, the azeotrope of water and the azeotropic agent is distilled out, the azeotropic agent is recovered, and the organic acid is collected, so as to achieve the purpose of separation and purification. Therefore, the azeotropic rectification will add a recovery section of the azeotropic agent to recover the azeotropic agent.

CN102153458A has disclosed a method for recovering a dilute organic acid through sec-butyl acetate extraction-azeotropic rectification. In this method, sec-butyl acetate is an extractant in an extraction tower and an azeotropic agent in an azeotropic rectification tower; part of the dilute organic acid is transported to the top of a packed extraction tower, and a small stream of reflux liquid at the top of the azeotropic rectification tower is transported to the bottom of the extraction tower as the extractant for countercurrent contact and extraction with the dilute organic acid at room temperature; an extract phase of sec-butyl acetate, the organic acid and a small amount of water is obtained at the top of the extraction tower; a raffinate phase, water containing a trace of organic acid, is obtained from the bottom of the tower and enters a solvent recovery tower; the extract phase in the extraction tower is transported to an upper part of the azeotropic rectification tower for further purification, and the other part of sec-butyl acetate is transported to the top of the azeotropic rectification tower. This application has the characteristic of high separation efficiency, a recovery rate of acetic acid is higher than 95%, and the content of the organic acid in wastewater is below 0.5%. This application can overcome the defects of a high reflux ratio and high energy consumption of a direct rectification method and increase the production capacity for recovery of the dilute organic acid. However, this method is only for low-concentration organic acid solutions, and does not involve high-concentration aqueous organic acid solutions.

SUMMARY

The following is a summary of the subject matter described herein in detail. This summary is not intended to limit the scope of the claims.

The object of the present application is to provide a method for linkage recovery of an organic acid in an aqueous organic acid solution. The method is simple, and has low energy consumption and a good recovery effect with respect to single recovery of a low-concentration aqueous organic acid solution. The method does not need to add an azeotropic agent and thus saves costs with respect to single recovery of a high-concentration aqueous organic acid solution. This coordination manner can make full use of a reagent during recovery, reduce energy consumption, and simplify a process.

To achieve this object, the present application adopts solutions below.

The present application provides a method for linkage recovery of an organic acid in an aqueous organic acid solution, including steps described below.

An organic acid solution with a concentration lower than 20 wt % and an extractant are subjected to countercurrent extraction together to obtain an extract phase and a raffinate phase; and the extract phase and an organic acid solution with a concentration higher than 70 wt % are subjected to azeotropic rectification together to recover the organic acid.

The concentration of the organic acid in the organic acid solution with a concentration lower than 20 wt % may be 0.5 wt %, 1 wt %, 2 wt %, 5 wt %, 8 wt %, 10 wt %, 12 wt %, 15 wt %, 18 wt % or 19 wt %, etc.; the concentration of the organic acid in the organic acid solution with a concentration higher than 70 wt % may be 71 wt %, 72 wt %, 75 wt %, 78 wt %, 80 wt %, 82 wt %, 85 wt % wt %, 88 wt %, 90 wt %, 92 wt %, 95 wt %, 98 wt %, or 99 wt %, etc.; the concentrations are not limited to the listed values, and other unlisted values within the preceding numerical ranges are also applicable.

As an optional solution of the present application, an organic acid solution with a concentration ranging from 20 wt % to 70 wt % is extracted and concentrated to a concentration higher than 70 wt % for recovery.

As an optional solution of the present application, the extractant is any one selected from the group consisting of an ester extractant, an organic phosphorus extractant, an organic amine extractant, a ketone extractant, and a combination of at least two selected therefrom; typical but non-limiting examples of the combination include a combination of the ester extractant and the organic phosphorus extractant, a combination of the organic phosphorus extractant and the organic amine extractant, a combination of the organic amine extractant and the ketone extractant, a combination of the ketone extractant and the organic phosphorus extractant, a combination of the organic amine extractant and the ketone extractant, or a combination of the ester extractant and the ketone extractant, etc.

Optionally, the ester extractant includes any one selected from the group consisting of ethyl acetate, n-propyl acetate, isopropyl acetate, n-butyl acetate, sec-butyl acetate, t-butyl acetate, ethyl n-valerate, glycerol acetate, and a combination of at least two selected therefrom; typical but non-limiting examples of the combination include a combination of ethyl acetate and n-propyl acetate, a combination of n-propyl acetate and isopropyl acetate, a combination of isopropyl acetate and n-butyl acetate, a combination of n-butyl acetate and sec-butyl acetate, a combination of sec-butyl acetate and t-butyl acetate, a combination of t-butyl acetate and ethyl n-valerate, a combination of ethyl n-valerate and glycerol acetate, or a combination of ethyl acetate, n-propyl acetate and sec-butyl acetate, etc.

Optionally, the organic phosphorus extractant includes trioctyl oxyphosphorus and/or tributyl phosphate.

Optionally, the organic amine extractant includes any one selected from the group consisting of trioctylamine, primary amine N1923, tertiary amine N235, and a combination of at least two selected therefrom; typical but non-limiting examples of the combination include a combination of trioctylamine and primary amine N1923, a combination of primary amine N1923 and tertiary amine N235, a combination of tertiary amine N235 and trioctylamine, or a combination of trioctylamine, primary amine N1923 and tertiary amine N235, etc.

Optionally, the ketone extractant is cyclohexanone.

As an optional solution of the present application, when the organic acid is formic acid, the extractant is the amine extractant and/or the organic phosphorus extractant and a diluent.

Optionally, when the organic acid is formic acid, the extractant includes any one selected from the group consisting of primary amine N1923, tertiary amine N235, tributyl phosphate, and a combination of at least two selected therefrom, and the diluent; typical but non-limiting examples of the combination include a combination of primary amine N1923 and tertiary amine N235, a combination of tertiary amine N235 and tributyl phosphate, a combination of tributyl phosphate and primary amine N1923, or a combination of primary amine N1923, tertiary amine N235 and tributyl phosphate, etc.

Optionally, when the organic acid is acetic acid or propionic acid, the extractant is any one selected from the group consisting of the organic phosphorus extractant, the organic amine extractant, the ester extractant, the ketone extractant, and a combination of at least two selected therefrom; typical but non-limiting examples of the combination include a combination of the organic phosphorus extractant and the organic amine extractant, a combination of the organic amine extractant and the ketone extractant, a combination of the organic amine extractant and the ester extractant, a combination of the ester extractant or the ketone extractant, a combination of the ketone extractant and the organic phosphorus extractant, or a combination of the organic phosphorus extractant, the organic amine extractant and the ketone extractant, etc.

Optionally, when the organic acid is acetic acid or propionic acid, the extractant includes any one selected from the group consisting of trioctyl oxyphosphorus, tributyl phosphate, trioctylamine, cyclohexanone, ethyl acetate, n-propyl acetate, isopropyl acetate, n-butyl acetate, sec-butyl acetate, t-butyl acetate, ethyl n-valerate, glycerol acetate, and a combination of at least two selected therefrom; typical but non-limiting examples of the combination include a combination of trioctyl oxyphosphorus and tributyl phosphate, a combination of tributyl phosphate and trioctylamine, a combination of trioctylamine and cyclohexanone, a combination of cyclohexanone and ethyl acetate, a combination of ethyl acetate and n-propyl acetate, a combination of n-propyl acetate and isopropyl acetate, a combination of isopropyl acetate and n-butyl acetate, a combination of n-butyl acetate and sec-butyl acetate, a combination of sec-butyl acetate and t-butyl acetate, a combination of t-butyl acetate and ethyl n-valerate, a combination of ethyl n-valerate and glycerol acetate, or a combination of ethyl acetate, n-propyl acetate and sec-butyl acetate, etc.

Optionally, when the organic acid is butyric acid, the extractant is the organic phosphorus extractant and/or the organic amine extractant and a diluent.

Optionally, when the organic acid is butyric acid, the extractant includes primary amine N1923 and/or tributyl phosphate and a diluent.

Optionally, the diluent is a halogenated hydrocarbon, optionally chloroform and/or 1,1,2-trichloroethane.

Optionally, a volume ratio of the extractant to the diluent is (1-10):1, for example, 1:1, 2:1, 3:1, 4:1, 5:1, 6:1, 7:1, 8:1, 9:1 or 10:1, etc. However, the volume ratio is not limited to the listed values, and other unlisted values within this numerical range are also applicable.

As an optional solution of the present application, a volume ratio of the organic acid solution with a concentration lower than 20 wt % to the extractant is 1:(0.5-5), for example, 1:0.5, 1:1, 1:1.5, 1:2, 1:2.5, 1:3, 1:3.5, 1:4, 1:4.5 or 1:5, etc. However, the volume ratio is not limited to the listed values, and other unlisted values within this numerical range are also applicable.

In the present application, when the organic acid is formic acid, a volume ratio of a formic acid solution with a concentration lower than 20 wt % to the extractant is optionally 1:4.

Optionally, the countercurrent extraction is performed under normal pressure and at a temperature of 20 to 70° C., for example, 20° C., 30° C., 40° C., 50° C., 60° C. or 70° C., etc. However, the temperature is not limited to the listed values, and other unlisted values within this numerical range are also applicable.

The countercurrent extraction in the present application may be performed in a packed extraction tower, where a packing height of the packed extraction tower is equivalent to a height of 20-30 theoretical plates. The organic acid solution with a concentration lower than 20 wt % enters the top of the packed extraction tower, the extractant enters the bottom of the packed extraction tower, and the countercurrent extraction is performed at normal temperature and under normal pressure, so as to obtain the extract phase at the top of the tower, and obtain the raffinate at the bottom of the tower.

Optionally, the extract phase includes the extractant, the organic acid and water.

In the present application, the concentration of the organic acid in the extract phase is 4-40 wt %, for example, 7 wt %, 10 wt %, 15 wt %, 20 wt %, 25 wt %, 30 wt %, 35 wt % or 40 wt %, etc.

However, the concentration is not limited to the listed values, and other unlisted values within this numerical range are also applicable.

Optionally, the raffinate phase includes water, the extractant and the organic acid.

In the present application, the concentration of the organic acid in the raffinate phase is 0.01-2.0 wt %, for example, 0.01 wt %, 0.05 wt %, 0.1 wt %, 0.2 wt %, 0.5 wt %, 0.8 wt %, 1.0 wt %, 1.5 wt %, 1.8 wt % or 2.0 wt %, etc. However, the concentration is not limited to the listed values, and other unlisted values within this numerical range are also applicable.

As an optional solution of the present application, a volume ratio of the organic acid solution with a concentration higher than 70 wt % to the extract phase is 1:(1-5), for example, 1:1, 1:1.5, 1:2, 1:2.5, 1:3, 1:3.5, 1:4, 1:4.5 or 1:5, etc. However, the volume ratio is not limited to the listed values, and other unlisted values within this numerical range are also applicable.

In the present application, the azeotropic rectification may be performed in an azeotropic rectification tower. A packing height of the azeotropic rectification tower is equivalent to 45 to 55 theoretical plates. The extract phase obtained through the countercurrent extraction enters the azeotropic rectification tower from the 20th to the 25th plates, and the organic acid solution with a concentration higher than 70 wt % enters the azeotropic rectification tower from the 30th to 35th plates, so that after the azeotropic rectification, the extractant, water and a small amount of organic acid are distilled out from the top of the tower, and the organic acid is obtained from the bottom of the tower. A distillate obtained from the top of the tower is separated, so that the extractant can be obtained and recycled.

As an optional solution of the present application, when the organic acid is acetic acid or propionic acid, an extractant for extraction and concentration includes any one selected from the group consisting of ethyl acetate, n-propyl acetate, isopropyl acetate, n-butyl acetate, sec-butyl acetate, t-butyl acetate, ethyl n-valerate, glycerol acetate, and a combination of at least two selected therefrom; typical but non-limiting examples of the combination include a combination of ethyl acetate and n-propyl acetate, a combination of n-propyl acetate and isopropyl acetate, a combination of isopropyl acetate and n-butyl acetate, a combination of n-butyl acetate and sec-butyl acetate, a combination of sec-butyl acetate and t-butyl acetate, a combination of t-butyl acetate and ethyl n-valerate, a combination of ethyl n-valerate and glycerol acetate, or a combination of ethyl acetate, n-propyl acetate and sec-butyl acetate, etc.

As an optional solution of the present application, when the organic acid is formic acid or butyric acid, the extractant for extraction and concentration is the same as the extractant for the countercurrent extraction.

As an optional solution of the present application, a solid adsorbent is used for purifying the aqueous organic acid solution before the countercurrent extraction.

Optionally, the solid adsorbent is used for adsorbing the raffinate phase, and the organic acid in the raffinate phase is recovered through heating and desorption while the adsorbent is regenerated.

The solid adsorbent used in the present application may be activated carbon, an anionic resin or a molecular sieve, etc.

As an optional solution of the present application, the method for linkage recovery of an organic acid in an aqueous organic acid solution includes steps described below.

An organic acid solution with a concentration lower than 20 wt % and an extractant at a volume ratio of 1:(1-3) are mixed and then subjected to countercurrent extraction under normal pressure at 20-25° C. to obtain an extract phase and a raffinate phase, where the raffinate phase is absorbed by a solid absorbent, and the organic acid in the raffinate phase is recovered through heating and desorption while the adsorbent is regenerated; and the extract phase and an organic acid solution with a concentration higher than 70 wt % at a volume ratio of (1-5):1 are mixed and then subjected to azeotropic rectification to recover the organic acid.

Compared with the related art, the present application has at least beneficial effects below.

The present application provides a method for linkage recovery of an organic acid in an aqueous organic acid solution. The method is simple, and has low energy consumption and a good recovery effect with respect to single recovery of a low-concentration aqueous organic acid solution. The method does not need to add an azeotropic agent and thus saves costs with respect to single recovery of a high-concentration aqueous organic acid solution. This coordination manner can make full use of the reagent during recovery, reduce energy consumption, and simplify the process.

Other aspects can be understood after the detailed description is read and understood.

DETAILED DESCRIPTION

For a better understanding of the present application, examples of the present application are listed below. Those skilled in the art should understand that the examples described herein are merely used for a better understanding of the present application and should not be construed as specific limitations to the present application.

In specific examples of the present application, a packed tower with a packing height equivalent to a height of 25 theoretical plates is used for countercurrent extraction under normal pressure at 25° C., an azeotropic rectification tower with a packing height of 50 theoretical plates is used for azeotropic rectification, an extract phase obtained through the countercurrent extraction enters the azeotropic rectification tower from the 23rd plate, and an organic acid solution with a concentration higher than 70 wt % enters the azeotropic rectification tower from the 32nd plate.

In Examples 1 to 5 of the present application, the volume ratio of the organic acid solution with a concentration lower than 20 wt % to the extractant is 1:2, the volume ratio of the organic acid solution with a concentration higher than 70 wt % to the extract phase is 1:3, and the extractant is trioctyl oxyphosphorus. The organic acid solution with a concentration lower than 20 wt % is simply referred to as a low-concentration aqueous organic acid solution, and the organic acid solution with a concentration higher than 70 wt % is simply referred to as a high-concentration aqueous organic acid solution. Concentrations of organic acid in the low-concentration aqueous organic acid solutions and high-concentration aqueous organic acid solutions are shown in Table 1. The organic acid is acetic acid.

TABLE 1

| No. | Low-concentration Aqueous Organic Acid Solution/wt % | High-concentration Aqueous Organic Acid Solution/wt % |
| --- | --- | --- |
| Example 1 | 2 | 95 |
| Example 2 | 5 | 90 |
| Example 3 | 10 | 85 |
| Example 4 | 12 | 80 |
| Example 5 | 15 | 75 |

The volume ratios of the low-concentration aqueous organic acid solutions to the extractant (simply referred to as a volume ratio A) and the volume ratios of the high-concentration aqueous organic acid solutions to the extract phases (simply referred to as a volume ratio B) in Examples 6 to 10 are different from those in Example 5, and other conditions in Examples 6 to 10 are the same as those in Example 4. The volume ratio As and the volume ratio Bs in Examples 6 to 10 are shown in Table 2.

TABLE 2

| No. | Volume Ratio A | Volume Ratio B |
| --- | --- | --- |
| Example 6 | 1:0.5 | 1:5 |
| Example 7 | 1:1 | 1:4 |
| Example 8 | 1:2 | 1:3 |
| Example 9 | 1:3 | 1:2 |
| Example 10 | 1:5 | 1:1 |

The extractants used in Examples 11 to 15 are different from that in Example 5, and other conditions in Examples 11 to 15 are the same as those in Example 5. The extractants used in Examples 11 to 15 are shown in Table 3.

TABLE 3

| No. | Extractant |
| --- | --- |
| Example 11 | Tributyl phosphate |
| Example 12 | Trioctylamine |
| Example 13 | Cyclohexanone |
| Example 14 | Trioctyl oxyphosphorus and trioctylamine (at a volume ratio of 1:1) |
| Example 15 | Trioctyl oxyphosphorus and tributyl phosphate (at a volume ratio of 1:1) |

In Examples 16 to 20, the high-concentration organic acid is obtained through extraction and concentration of the aqueous organic acid solution with a concentration ranging from 20 wt % to 70 wt %, and other conditions in Examples 16 to 20 are the same as those in Example 5. The organic acid concentrations and extractants selected for extraction and concentration are shown in Table 4.

TABLE 4

| No. | Organic Acid Concentration/wt % | Extractant |
| --- | --- | --- |
| Example 16 | 25 | N-propyl acetate |
| Example 17 | 30 | Sec-butyl acetate |
| Example 18 | 40 | T-butyl acetate |
| Example 19 | 50 | Ethyl n-valerate |
| Example 20 | 60 | Ethyl acetate and sec-butyl acetate (at a volume ratio of 1:1) |

In Examples 21 to 25, the organic acid is formic acid; except for the selection of the extractant, the selection of the extractant for extraction and concentration, and that a diluent is added during the extraction of a low-concentration organic acid, other conditions are the same as those in Examples 16 to 20. The extractant is the same as the extractant for extraction and concentration. The selection of extractants and diluents is shown in Table 5.

TABLE 5

| No. | Diluent | Extractant | Volume Ratio of the Diluent to the Extractant |
| --- | --- | --- | --- |
| Example 21 | Chloroform | Primary amine N1923 | 10:1 |
| Example 22 | 1,1,2-Trichloroethane | Tertiary amine N235 | 8:1 |
| Example 23 | Chloroform | Tributyl phosphate | 5:1 |
| Example 24 | 1,1,2-Trichloroethane | Tributyl phosphate | 2:1 |
| Example 25 | Chloroform and 1,1,2-trichloroethane (at a volume ratio of 1:1) | Primary amine N1923 and tertiary amine N235 (at a volume ratio of 1:1) | 1:1 |

In Comparative Examples 1 to 5, concentrations of the organic acid in the low-concentration aqueous organic acid solutions are different from that in Example 5, and other conditions are the same as those in Example 5. In Comparative Examples 6 to 10, concentrations of the organic acid in the high-concentration aqueous organic acid solutions are different from that in Example 5, and other conditions are the same as those in Example 4. In Comparative Examples 11 to 15, concentrations of the organic acid in the low-concentration aqueous organic acid solutions and the high-concentration aqueous organic acid solutions are different from those in Example 5, and other conditions are the same as those in Example 5. The concentrations of the organic acid in the low-concentration aqueous organic acid solutions and the high-concentration aqueous organic acid solutions in Comparative Examples 1 to 5 are shown in the following Table 4. The concentrations of the organic acid in the low-concentration aqueous organic acid solutions and the high-concentration aqueous organic acid solutions in Comparative Examples 6 to 10 are shown in the following Table 5. The concentrations of the organic acid in the low-concentration aqueous organic acid solutions and the high-concentration aqueous organic acid solutions in Comparative Examples 11 to 15 are shown in the following Table 6.

TABLE 4

| No. | Low-concentration Aqueous Organic Acid Solution/wt % | High-concentration Aqueous Organic Acid Solution/wt % |
| --- | --- | --- |
| Comparative Example 1 | 25 | 75 |
| Comparative Example 2 | 30 | 75 |
| Comparative Example 3 | 35 | 75 |
| Comparative Example 4 | 40 | 75 |
| Comparative Example 5 | 45 | 75 |

TABLE 5

| No. | Low-concentration Aqueous Organic Acid Solution/wt % | High-concentration Aqueous Organic Acid Solution/wt % |
| --- | --- | --- |
| Comparative Example 6 | 15 | 68 |
| Comparative Example 7 | 10 | 65 |
| Comparative Example 8 | 15 | 60 |
| Comparative Example 9 | 15 | 55 |
| Comparative Example 10 | 15 | 50 |

TABLE 6

| No. | Low-concentration Aqueous Organic Acid Solution/wt % | High-concentration Aqueous Organic Acid Solution/wt % |
| --- | --- | --- |
| Comparative Example 11 | 25 | 68 |
| Comparative Example 12 | 30 | 65 |
| Comparative Example 13 | 35 | 60 |
| Comparative Example 14 | 40 | 55 |
| Comparative Example 15 | 45 | 50 |

The organic acid in Examples 1 to 20 and Comparative Examples 1 to 15 is acetic acid. The purities and the extraction rates of the organic acid obtained in Examples 1 to 20 and Comparative Examples 1 to 15 are characterized, and results are shown in the following Table 6.

TABLE 6

| No. | Purity of Acetic Acid/% | Extraction Rate of Acetic Acid/% |
| --- | --- | --- |
| Example 1 | 98.0 | 98 |
| Example 2 | 98.5 | 97 |
| Example 3 | 97.8 | 97 |
| Example 4 | 98.4 | 98 |
| Example 5 | 99.0 | 96 |
| Example 6 | 96.0 | 96 |
| Example 7 | 96.5 | 97 |
| Example 8 | 98.0 | 97 |
| Example 9 | 97.5 | 98 |
| Example 10 | 96.0 | 96 |
| Example 11 | 97.0 | 97 |
| Example 12 | 96.3 | 98 |
| Example 13 | 97.5 | 98 |
| Example 14 | 98.4 | 97 |
| Example 15 | 99.0 | 98 |
| Example 16 | 96.5 | 98 |
| Example 17 | 98.2 | 97 |
| Example 18 | 97.5 | 99 |
| Example 19 | 99.1 | 97 |
| Example 20 | 98.3 | 98 |
| Comparative Example 1 | 78 | 81 |
| Comparative Example 2 | 80 | 83 |
| Comparative Example 3 | 84 | 80 |
| Comparative Example 4 | 76 | 79 |
| Comparative Example 5 | 81 | 84 |
| Comparative Example 6 | 81 | 76 |
| Comparative Example 7 | 74 | 72 |
| Comparative Example 8 | 71 | 77 |
| Comparative Example 9 | 82 | 74 |
| Comparative Example 10 | 79 | 74 |
| Comparative Example 11 | 75 | 75 |
| Comparative Example 12 | 84 | 79 |
| Comparative Example 13 | 82 | 80 |
| Comparative Example 14 | 76 | 71 |
| Comparative Example 15 | 77 | 74 |

The purities and the extraction rates of formic acid obtained in Examples 21 to 25 are characterized, and results are shown in the following Table 7.

TABLE 7

| No. | Purity of Formic Acid/% | Extraction Rate of Formic Acid/% |
| --- | --- | --- |
| Example 21 | 95.6 | 95 |
| Example 22 | 98.8 | 96 |
| Example 23 | 96.0 | 94 |
| Example 24 | 97.5 | 98 |
| Example 25 | 95.7 | 95 |

As can be seen from test results in Table 1, when the organic acid is directly extracted from a low-concentration organic acid solution with a concentration greater than 20 wt % and/or a high-concentration organic acid solution with a concentration less than 70 wt %, the extraction rate of the organic acid and the purity of the organic acid are both lower than those of the organic acid extracted by the method of the present application.

The applicant has stated that although the detailed process equipment and flows of the present application are described through the examples described above, the present application is not limited to the detailed process equipment and flows described above, which means that the implementation of the present application does not necessarily depend on the detailed process equipment and flows described above.

What is claimed is:

1. A method for linkage recovery of an organic acid in an aqueous organic acid solution, comprising:
    mixing an aqueous organic acid solution with a concentration lower than 20 wt % and an extractant and then subjecting the mixture to countercurrent extraction to obtain an extract phase and a raffinate phase;
    providing an aqueous organic acid solution with a concentration ranging from 20 wt % to 70 wt % and extracting and concentrating the solution to provide an aqueous organic acid solution with a concentration higher than 70 wt %; and
    subjecting the extract phase and the aqueous organic acid solution with a concentration higher than 70 wt % to azeotropic rectification together to recover the organic acid;
    wherein a volume ratio of the aqueous organic acid solution with a concentration lower than 20 wt % to the extractant is 1:0.5-5; and
    wherein a volume ratio of the aqueous organic acid solution with a concentration higher than 70 wt % to the extract phase is 1: 1-5.

2. The method according to claim 1, wherein the extractant in the counter current extraction of the aqueous organic acid solution with a concentration lower than 20 wt % is any one selected from the group consisting of an ester extractant, an organic phosphorus extractant, an organic amine extractant, a ketone extractant, and a combination of at least two selected therefrom.

3. The method according to claim 2, wherein the organic acid is formic acid, and the extractant in the counter current extraction of the aqueous organic acid solution with a concentration lower than 20 wt % is the organic amine extractant and/or the organic phosphorus extractant, and wherein the mixture of the aqueous organic acid solution with a concentration lower than 20 wt % and the extractant further comprises a diluent.

4. The method according to claim 1, wherein the organic acid is acetic acid or propionic acid, and an extractant for extraction of the aqueous organic acid solution with a concentration ranging from 20 wt % to 70 wt % comprises any one selected from the group consisting of ethyl acetate, n-propyl acetate, isopropyl acetate, n-butyl acetate, sec-butyl acetate, t-butyl acetate, ethyl n-valerate, glycerol acetate, and a combination of at least two selected therefrom.

5. The method according to claim 1, wherein the organic acid is formic acid, and the extractant for extraction of the aqueous organic acid solution with a concentration ranging from 20 wt % to 70 wt % is the same as the extractant for the countercurrent extraction.

6. The method according to claim 1, wherein an adsorbent is used for purifying the aqueous organic acid solution before the countercurrent extraction;
    a solid adsorbent is used for adsorbing organic acid in the raffinate phase, and the organic acid in the raffinate phase is recovered through heating and desorption while the adsorbent is regenerated.

7. The method according to claim 1, comprising:
    mixing an aqueous organic acid solution with a concentration lower than 20 wt % and an extractant at a volume ratio of 1:0.5-5 and then subjecting the mixture to countercurrent extraction under normal pressure at 20-25° C. to obtain an extract phase and a raffinate phase, wherein organic acid in the raffinate phase is adsorbed by a solid adsorbent, and the organic acid in the raffinate phase is recovered through heating and desorption while the adsorbent is regenerated; and the extract phase and the aqueous organic acid solution with a concentration higher than 70 wt % are mixed at a volume ratio of 1-5:1 and then subjected to azeotropic rectification to recover the organic acid.

8. The method of claim 1, wherein the countercurrent extraction is performed under normal pressure and at a temperature of 20 to 70° C.

9. The method of claim 1, wherein the extract phase comprises the extractant, the organic acid and water, and the raffinate phase comprises water, the extractant and the organic acid.

10. The method of claim 2, wherein the ester extractant comprises any one selected from the group consisting of ethyl acetate, n-propyl acetate, isopropyl acetate, n-butyl acetate, sec-butyl acetate, t-butyl acetate, ethyl n-valerate, glycerol acetate, and a combination of at least two selected therefrom.

11. The method of claim 2, wherein the organic phosphorus extractant comprises trioctyl oxyphosphorus and/or tributyl phosphate.

12. The method of claim 2, wherein the organic amine extractant comprises any one selected from the group consisting of trioctylamine, primary amine N1923, tertiary amine N235, and a combination of at least two selected therefrom.

13. The method of claim 2, wherein the ketone extractant is cyclohexanone.

14. The method of claim 2, wherein the organic acid is acetic acid or propionic acid, and the extractant is any one selected from the group consisting of the organic phosphorus extractant, the organic amine extractant, the ester extractant, the ketone extractant, and a combination of at least two selected therefrom.

15. The method of claim 2, wherein the organic acid is butyric acid, and the extractant in the counter current extraction of the aqueous organic acid solution with a concentration lower than 20 wt % is the organic phosphorus extractant and/or is the organic amine extractant and the extractant further comprises a diluent.

16. The method of claim 3, wherein the diluent is a halogenated hydrocarbon and the volume ratio of the extractant to the diluent is 1-10:1.

17. The method of claim 15, wherein the diluent is a halogenated hydrocarbon and the volume ratio of the extractant to the diluent is 1-10:1.

\* \* \* \* \*